US009579163B2

(12) United States Patent
Valdastri et al.

(10) Patent No.: US 9,579,163 B2
(45) Date of Patent: Feb. 28, 2017

(54) ROBOTIC PLATFORM FOR MINI-INVASIVE SURGERY

(76) Inventors: Pietro Valdastri, Nashville, TN (US); Christian Di Natali, Nashville, TN (US); Massimiliano Simi, Leghorn (IT); Tommaso Ranzani, Pisa (IT); Arianna Menciassi, Pontedera (Pisa) (IT); Paolo Dario, Leghorn (IT)

( * ) Notice: Subject to any disclaimer, the term of this patent is extended or adjusted under 35 U.S.C. 154(b) by 532 days.

(21) Appl. No.: 14/122,826

(22) PCT Filed: May 31, 2012

(86) PCT No.: PCT/IB2012/052739
§ 371 (c)(1),
(2), (4) Date: Mar. 6, 2014

(87) PCT Pub. No.: WO2012/164517
PCT Pub. Date: Dec. 6, 2012

(65) Prior Publication Data
US 2014/0358162 A1 Dec. 4, 2014

(30) Foreign Application Priority Data
May 31, 2011 (IT) .............................. FI2011A0114

(51) Int. Cl.
*A61B 19/00* (2006.01)
*A61B 17/00* (2006.01)
*G05B 15/02* (2006.01)

(52) U.S. Cl.
CPC ........ *A61B 34/30* (2016.02); *A61B 17/00234* (2013.01); *A61B 34/71* (2016.02);
(Continued)

(58) Field of Classification Search
CPC ......... A61B 34/70; A61B 34/73; A61B 34/30; A61B 34/37; A61B 2034/302; A61B 34/00;
(Continued)

(56) References Cited

U.S. PATENT DOCUMENTS 3,315,660 A 4/1967 Abella
3,858,572 A 1/1975 Binard et al.
(Continued)

FOREIGN PATENT DOCUMENTS

DE 102006019419 11/2007
EP 2163206 3/2010
(Continued)

OTHER PUBLICATIONS

P. Valdastri, S. Tognarelli, A. Menciassi, P. Dario, "A scalable platform for biomechanical studies of tissue cutting forces", Measurement Science and Technology, 2009, vol. 20, 045801 (11pp).
(Continued)

*Primary Examiner* — David C Eastwood
*Assistant Examiner* — Mikail Mannan
(74) *Attorney, Agent, or Firm* — Michael Best & Friedrich LLP

(57) ABSTRACT

Robotic platform for mini-invasive surgery comprising robotic arms (4a, 4b) suitable to be placed in the body of a patient, introduced through a single access port, which are an extension of external robotic manipulators (19). The continuity between external (1) and internal (4a, 4b) robotic arms is guaranteed by means of a trans-abdominal magnetic connection (6) between the internal robotic arm integral with the external one. The trans-abdominal magnetic coupling not only guarantees a stable anchoring, but most of all it transfers degrees of freedom to the internal robotic arms, inducing the motion of internal magnets by means of the
(Continued)

automatized motion of external magnets. It is also possible to reposition the internal robotic arms without requiring having to additionally perform incisions on the abdomen. Using the external robotic arms allows translating the internal ones on the entire abdomen thus providing a working space not bound to the point of insertion and theoretically unlimited.

17 Claims, 6 Drawing Sheets

(52) U.S. Cl.
CPC .............. *G05B 15/02* (2013.01); *A61B 90/30* (2016.02); *A61B 2017/00464* (2013.01); *A61B 2017/00477* (2013.01); *A61B 2017/00876* (2013.01); *A61B 2034/302* (2016.02); *A61B 2034/731* (2016.02)

(58) Field of Classification Search
CPC .............. A61B 34/10; A61B 2034/101; A61B 2034/102; A61B 2034/104; A61B 2034/105; A61B 2034/107; A61B 2034/108; A61B 34/20; A61B 2034/2046; A61B 2034/2048; A61B 2034/2051; A61B 2034/2053; A61B 2034/2055; B25J 15/0246; B25J 7/00; B25J 9/0018
See application file for complete search history.

(56) References Cited

U.S. PATENT DOCUMENTS

| | | | |
|---|---|---|---|
| 3,870,072 | A | 3/1975 | Lindemann |
| 4,048,992 | A | 9/1977 | Lindemann et al. |
| 4,207,887 | A | 6/1980 | Hiltebrandt et al. |
| 5,489,256 | A | 2/1996 | Adair |
| 6,248,080 | B1 | 6/2001 | Miesel et al. |
| 6,270,787 | B1 | 8/2001 | Ayer |
| 6,802,811 | B1 | 10/2004 | Slepian |
| 7,722,559 | B2 | 5/2010 | Uesugi et al. |
| 2001/0051766 | A1 | 12/2001 | Gazdzinski |
| 2003/0114731 | A1 | 6/2003 | Cadeddu et al. |
| 2005/0277852 | A1 | 12/2005 | Shih et al. |
| 2008/0015413 | A1 | 1/2008 | Barlow et al. |
| 2008/0021334 | A1 | 1/2008 | Finburgh et al. |
| 2008/0058835 | A1 | 3/2008 | Farritor et al. |
| 2008/0154093 | A1 | 6/2008 | Cho et al. |
| 2008/0207999 | A1 | 8/2008 | Abraham-Fuchs et al. |
| 2009/0024142 | A1* | 1/2009 | Ruiz Morales .......... B25J 9/041 606/130 |
| 2009/0054877 | A1 | 2/2009 | Hood et al. |
| 2009/0054909 | A1* | 2/2009 | Farritor .............. A61B 19/2203 606/130 |
| 2009/0171268 | A1 | 7/2009 | Williams, Jr. et al. |
| 2009/0171373 | A1 | 7/2009 | Farritor et al. |
| 2009/0292205 | A1 | 11/2009 | Osaka |
| 2010/0100117 | A1 | 4/2010 | Brister et al. |
| 2010/0198008 | A1 | 8/2010 | Kawano |
| 2010/0256636 | A1 | 10/2010 | Fernandez et al. |
| 2011/0184235 | A1 | 7/2011 | Schostek et al. |
| 2011/0202070 | A1 | 8/2011 | Dario et al. |
| 2011/0301497 | A1 | 12/2011 | Shachar et al. |
| 2011/0313415 | A1 | 12/2011 | Fernandez et al. |
| 2012/0035416 | A1 | 2/2012 | Fernandez et al. |
| 2012/0041345 | A1 | 2/2012 | Rajamani et al. |
| 2012/0149981 | A1 | 6/2012 | Khait et al. |
| 2012/0271555 | A1 | 10/2012 | Levental et al. |
| 2013/0131695 | A1 | 5/2013 | Scarfogliero et al. |
| 2013/0165859 | A1 | 6/2013 | Imran |
| 2013/0225922 | A1 | 8/2013 | Schentag et al. |
| 2013/0298715 | A1 | 11/2013 | Valdastri et al. |
| 2013/0324914 | A1 | 12/2013 | Valdastri et al. |

FOREIGN PATENT DOCUMENTS

| | | |
|---|---|---|
| EP | 2286756 | 2/2011 |
| WO | 0030548 | 6/2000 |
| WO | 2004041068 | 5/2004 |
| WO | 2007013059 | 2/2007 |
| WO | 2007146987 | 12/2007 |
| WO | 2008122997 | 10/2008 |
| WO | 2009014917 | 1/2009 |
| WO | 2010042611 | 4/2010 |
| WO | 2010044053 | 4/2010 |
| WO | 2010046823 | 4/2010 |
| WO | 2011058505 | 5/2011 |
| WO | 2011135503 | 11/2011 |
| WO | 2012028557 | 3/2012 |
| WO | 2012035157 | 3/2012 |
| WO | 2012080947 | 6/2012 |
| WO | 2012164517 | 12/2012 |
| WO | 2013027182 | 2/2013 |

OTHER PUBLICATIONS

E. Buselli, P. Valdastri, M. Quirini, A. Menciassi, P. Dario, "Superelastic leg design optimization for an endoscopic capsule with active locomotion", Smart Materials and Structures, 2009, vol. 18, 015001 (8pp).

P. Valdastri, C. Quaglia, E. Susilo, A. Menciassi, P. Dario, C.N. Ho, G. Anhoeck, M.O. Schurr, "Wireless Therapeutic Endoscopic Capsule: in-vivo Experiment", Endoscopy, 2008, vol. 40, pp. 979-982.

P. Valdastri, A. Menciassi, P. Dario, "Transmission Power Requirements for Novel ZigBee Implants in the Gastrointestinal Tract", IEEE Transactions on Biomedical Engineering, 2008, vol. 55, No. 6, pp. 1705-1710.

P. Valdastri, S. Rossi, A. Menciassi, V. Lionetti, F. Bernini, F. A. Recchia, P. Dario, "An Implantable ZigBee Ready Telemetric Platform for In Vivo Monitoring of Physiological Parameters", Sensors and Actuators A: Physical, 2008, vol. 142, No. 1, pp. 369-378.

A. Sieber, P. Valdastri, K. Houston, C. Eder, O. Tonet, A. Menciassi, P. Dario, "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.

A. Sieber, P. Valdastri, K. Houston, A. Menciassi, P. Dario, "Flip Chip Microassembly of a Silicon Triaxial Force Sensor on Flexible Substrates", Sensors and Actuators A: Physical, 2008, vol. 142, No. 1, pp. 421-428.

L. Beccai, S. Roccella, L. Ascari, P. Valdastri, A. Sieber, M. C. Carrozza, P. Dario, "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168.

C. Oddo, P. Valdastri, L. Beccai, S. Roccella, M.C. Carrozza, P. Dario, "Investigation on calibration methods for multi-axis, linear and redundant force sensors", Measurement Science and Technology, 2007, vol. 18, pp. 623-631.

P. Valdastri, K. Houston, A. Menciassi, P. Dario, A. Sieber, M. Yanagihara, M. Fujie, "Miniaturised Cutting Tool with Triaxial Force Sensing Capabilities for Minimally Invasive Surgery", ASME Journal of Medical Devices, 2007, vol. 1, N. 3, pp. 206-211.

G. Turchetti, B. Labella, P. Valdastri, A. Menciassi, P. Dario, "The importance of giving an alternative: the case of fetal surgery", Int. J. Healthcare Technology and Management, 2007, vol. 8, Nos. 3-4, pp. 250-267.

P. Valdastri, K. Harada, A. Menciassi, L. Beccai, C. Stefanini, M. Fujie, and P. Dario, "Integration of a Miniaturised Triaxial Force Sensor in a Minimally Invasive Surgical Tool", IEEE Transactions on Biomedical Engineering, 2006, vol. 53, No. 11, 2397-2400.

P. Valdastri, P. Corradi, A. Menciassi, T. Schmickl, K. Crailsheim, J. Seyfried, P. Dario, "Micromanipulation, Communication and Swarm Intelligence Issues in a Swarm Microrobotic Platform", Robotics and Autonomous Systems, 2006, vol. 54, No. 10, pp. 789-804.

(56) References Cited

OTHER PUBLICATIONS

P. Valdastri, S. Roccella, L. Beccai, E. Cattin, A. Menciassi, M. C. Carrozza, P. Dario, "Characterization of a novel hybrid silicon three-axial force sensor", Sensors and Actuators A: Physical, 2005, vol. 123-124C, pp. 249-257.

L. Beccai, S. Roccella, A. Arena, F. Valvo, P. Valdastri, A. Menciassi, M. C. Carrozza, P. Dario, "Design and fabrication of a hybrid silicon three axial force sensor for biomechanical applications", Sensors and Actuators A: Physical, 2005, vol. 120, No. 2, pp. 370-382.

P. Valdastri, A. Menciassi, A. Arena, C. Caccamo, and P. Dario, "An Implantable Telemetry Platform System for in vivo Monitoring of Physiological Parameters", IEEE Transactions on Information Technology in Biomedicine, 2004, vol. 8, No. 3, pp. 271-278.

X. Wang, C. Di Natali, M. Beccani, M. Kern, P. Valdastri, M. Rentschler, "Novel Medical Wired Palpation Device: A Device Validation Study of Material Properties", Transducers 2013, Barcelona, Spain, pp. 1653-1658.

M. Beccani, C. Di Natali, M. E. Rentschler, P. Valdastri, "Wireless Tissue Palpation: Proof of Concept for a Single Degree of Freedom", IEEE International Conference on Robotics and Automation (ICRA) 2013, Karlsruhe, Germany, pp. 703-709.

M. Beccani, C. Di Natali, M. Rentschler, P. Valdastri, "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).

C. Di Natali, P. Valdastri "Remote active magnetic actuation for a single-access surgical robotic manipulator", in Proc. of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.

C. Di Natali, T. Ranzani, M. Simi, A. Menciassi, P. Valdastri "Trans-abdominal Active Magnetic Linkage for Robotic Surgery: Concept Definition and Model Assessment", in Proc. of IEEE International Conference on Robotics and Automation (ICRA) 2012, St Paul, MN, USA, May 2012, pp. 695-700.

T. Ranzani, C. Di Natali, M. Simi, A. Menciassi, P. Dario, P. Valdastri, "A Novel Surgical Robotic Platform Minimizing Access Trauma", in Proc. of 4th Hamlyn Symposium on Medical Robotics, London, UK, Jun. 2011, pp. 15-16.

P. Valdastri, G. Ciuti, A. Verbeni, A. Menciassi, P. Dario, A. Arezzo, M. Morino, "Magnetic air capsule robotic system: a novel approach for painless colonoscopy", 19th International Congress of the European Association of Endoscopic Surgery (EAES) in Turin, Italy.

M. Simi, G. Sardi, P. Valdastri, A. Menciassi, P. Dario, "Magnetic Levitation Camera Robot for Endoscopic Surgery", in Proc. of IEEE International Conference on Robotics and Automation (ICRA) 2011, Shanghai, China, May 2011, pp. 5279-5284.

O. Alonso, J. Canals, L. Freixas, J. Samitier, A. Dieguez, M. Vatteroni, E. Susilo, C. Cavallotti, P. Valdastri, "Enabling multiple robotic functions in an endoscopic capsule for the entire gastrointestinal tract exploration", in Proc. ESSCIRC, 2010, pp. 386-389.

J. L. Toennies, G. Ciuti, B. F. Smith, A. Menciassi, P. Valdastri, and Robert J. Webster III, "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.

G. Tortora, S. Caccavaro, P. Valdastri, A. Menciassi, P. Dario, "Design of an autonomous jellyfish miniature robot based on a novel concept of magnetic actuation", in Proc. of IEEE International Conference on Robotics and Automation (ICRA) 2010, Anchorage, AK, USA, May 2010, pp. 1592-1597.

L. S. Chiang, P. S. Jay, P. Valdastri, A. Menciassi, P. Dario, "Tendon Sheath Analysis for Prediction of Distal End Force and Elongation", in Proc. IEEE/ASME Conference on Advanced Intelligent Mechatronics 2009, Singapore, Jul. 2009, pp. 332-337.

O. Tonet, M. Marinelli, G. Megali, A. Sieber, P. Valdastri, A. Menciassi, P. Dario, "Control of a teleoperated nanomanipulator with time delay under direct vision feedback", in Proc. of IEEE International Conference on Robotics and Automation (ICRA) 2007, Rome, Italy, Apr. 2007, pp. 3514-3519.

J. L. Toennies, R. J. Webster III, P. Valdastri, "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).

A. Menciassi, P. Valdastri, K. Harada, P. Dario, "Single and Multiple Robotic Capsules for Endoluminal Diagnosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 978-1-4419-1125-4.

B. Laulicht, N. Gidmark, A. Tripathl, E. Mathiowitz, "Localization of magnetic pills," Proc. of the National Academy of Sciences, vol. 108, No. 6, 2252-2257 (Feb. 8, 2011).

S. Best, E. Olweny, S. Park, P. Smith, R. Fernandez, D. Scott, R. Bergs, and J. Cadeddu. New generation magnetic camera facilities porcine LESS nephrectomy. The Journal of Urology, 185:e413-413, 2011.

PCT International Search Report and Written Opinion for Application No. PCT/US2015/049142 dated Dec. 11, 2015.

M. Simi, G. Gerboni, A. Menciassi, P. Valdastri, "Magnetic Mechanism for Wireless Capsule Biopsy", in Proc. of ASME Design of Medical Devices Conference, Apr. 10-12, 2012, Minneapolis, MN, ASME Journal of Medical Devices, vol. 6, p. 017611-1.

F. Carpi, N. Kastelein, M.Talcott, and C.Pappone. Magnetically controllable gastrointestinal steering ofvideo capsules. IEEE Transactions on Biomedical Engineering, 58:231-234, 2011.

J. Keller, C. Fibbe, F. Volke, J. Gerber, A. C. Mosse, M. Reimann-Zawadzki, E. Rabinovitz, P. Layer,D. S. and V. Andresen, U. Rosien, and P. Swain. Inspection of the human stomach using remote controlled capsule endoscopy: a feasibility study in healthy volunteers. Gastrointestinal Endoscopy,73:22-28, 2011.

S. Park, R. Bergs, R. Eberhart, L. Baker, R. Fernandez, and J. Cadeddu. Trocar-less instrumentation forlaparoscopy: magnetic positioning of intra-abdominal camera and retractor. Annals of Surgery,245:379-384, 2007.

J. F. Rey, H. Ogata, N. Hosoe, K. Ohtsuka, N. Ogata, K. Ikeda, H. Aihara, I. Pangtay, T. Hibi, S. Kudo,and H. Tajiri. Feasibility of stomach exploration with a guided capsule endoscope. Endoscopy, 42:541-545, 2010.

P. Swain, R. Austin, K. Bally, and R. Trusty. Development and testing of a tethered, independentcamera for Notes and single-site laparoscopic procedures. Surgical Endoscopy, 24:2013-2021, 2010.

P. Valdastri, G. Ciuti, A. Verbeni, A. Menciassi, P. Dario, A. Arezzo, M. Morino. Magnetic air capsulerobotic system: Proof of concept of a novel approach for painless colonoscopy. Surgical Endoscopy,2011, in press.

G. Ostrovsky, Preview of Magnetically Guided Colonoscopy from Vanderbilt. MedGadget press release:http://medgadget.com/2011/10/preview-of-magnetically-guided-colonoscopy-from-vanderbilt.html.

A. Fritscher-Ravens, S. Fox, C.P. Swain, P. Mills, and G. Long. Cathcam guide wire-directedcolonoscopy: first pilot study in patients with a previous incomplete colonoscopy. Endoscopy, 38:209-213, 2006.

B. Vucelic, D. Rex, R. Pulanic, J. Rider, I. Hrstic, B. Levin, Z. Halpern, and N. Arber. The Aer-o-Scope: proof of concept of a pneumatic, skill-independent, self-propelling, self-navigating colonoscope.Gastroenterology, 130:672-677, 2006.

F. Cosentino, E. Tumino, G.R. Passoni, E. Morandi, and A. Capria. Functional evaluation of theEndotics System, a new disposable self-propelled robotic colonoscope: in vitro tests and clinical trial. International Journal of Artificial Organs, 32:517-527, 2009.

M. Shike, Z. Fireman, R. Eliakim, O. Segol, A. Sloyer, L.B. Cohen, S. Goldfarb-Albak, and A. Repici.Sightline Colonosight system for a disposable, power-assisted, non-fiber-optic colonoscopy.Gastrointestinal Endoscopy, 68:701-710, 2008.

T. Rösch, A. Adler, H. Pohl, E. Wettschureck, M. Koch, B. Wiedenmann, and N. Hoepner. A motor-driven single-use

(56) References Cited

OTHER PUBLICATIONS colonoscope controlled with a hand-held device: a feasibility study involunteers. Gastrointestinal Endoscopy, 67:1139-1146, 2008.
A. Eickhoff, J. Van Dam, R. Jakobs, V. Kudis, D. Hartmann, U. Damian, U. Weickert, D. Schilling, andJ.F. Riemann. Computer-assisted colonoscopy (the NeoGuide endoscopy system): results of the firsthuman clinical trial (pace study). The American Journal of Gastroenterology, 102:261-266, 2007.
M. Moshkowitz, Y. Hirsch, I. Carmel, T. Duvdevany, I. Fabian, E.P. Willenz, and J. Cohen. A noveldevice for rapid cleaning of poorly prepared colons. Endoscopy, 42:834-836, 2010.
A. Fritscher-Ravens, C. Mosse, T. Mills, K. Ikeda, P. Swain, Colon cleaning during colonoscopy: a newmechanical cleaning device tested in a porcine model. Gastrointestinal Endoscopy, 63:141-143, 2006.
H. Richert, B. Hilgenfeld, and P. Gomert, "Magnetic sensor techniques for new intelligent endoscopic capsules," http://www.vector-project.com/press/artikel/VECTOR%20article_Richert_MagneticSensorTechniques.pdf, publicly available prior to Sep. 17, 2012.
Than, T. D.; Alici, G.; Zhou, H.; Li, W.; "A Review of Localization Systems for Robotic Endoscopic Capsules," Biomedical Engineering, IEEE Transactions on , vol. 59, No. 9, pp. 2387-2399, Sep. 2012.
NDI Medical's Aurora product, http://www.ndigital.com/medical/products/aurora/, publicly available prior to Sep. 17, 2012.
M. B. H. Gerald Rogers. The safety of carbon dioxide insufflation during colonoscopic electro-surgical polypectomy. Gastrointestinal Endoscopy, 20:115-117, 1974.
Bracco. Co2 efficient endoscopic insufflator.
P. E. J.-M. D. Filip Janssens, Jacques Deviere. Carbon dioxide for gut distension duringdigestive endoscopy: Technique and practice survey. World Journal of Gastroenterology, 15(12):1475-1479, 2009.
F. A. Macrae, K. G. Tan, and C. B. Williams. Towards safer colonoscopy: a report on thecomplications of 5000 diagnostic or therapeutic colonoscopies. Gut, 24(5):376{383, 1983.
W. J. R. P. Phaosawasdi K, Cooley W. Carbon dioxide-insufflated colonoscopy: an ignoredsuperior technique. Gastrointestinal Endoscopy, 32:330-333, 1986.
K. Sumanac, I. Zealley, B. M. Fox, J. Rawlinson, B. Salena, J. K. Marshall, G. W. Stevenson,and R. H. Hunt. Minimizing postcolonoscopy abdominal pain by using fCO2g insufflation: Aprospective, randomized, double blind, controlled trial evaluating a new commercially availablefCO2g delivery system. Gastrointestinal Endoscopy, 56(2):190-194, 2002.
J. C. H. Wong, K. K. Yau, H. Y. S. Cheung, D. C. T. Wong, C. C. Chung, and M. K W. Li.Towards painless colonoscopy: A randomized controlled trial on carbon dioxide-insufflatingcolonoscopy. ANZ Journal of Surgery, 78 (10):871-874, 2008.
PCT International Search Report and Written Opinion for Application No. PCT/EP2011/064764 dated Oct. 10, 2011.
PCT International Search Report and Written Opinion for Application No. PCT/US2014/012086 dated May 14, 2014.
PCT International Search Report and Written Opinion for Application No. PCT/IB2012/052739 dated Aug. 7, 2012.
Toennies, J.L. et al., "A Wireless Insufflation System for Capsular Endoscopes," Journal of Medical Devices, vol. 3 (Jun. 2009).
Toennies, Jenna L. et al., "Initial Feasibility Studies on Wireless Insufflation of the GI Tract," IEEE International Conference on Robotics and Automation 2010—Workshop on Meso-ScaleRobotics for Medical Interventions, (May 3, 2010).
Smith, Byron, "Wireless Insufflation for Wireless Capsule Endoscopy," Vanderbilt University Master's Thesis (Aug. 2012).
Pedersen, Amanda, "Capsule Endoscopy in ER Could Drop Admission Rate," Medical Device Daily (Feb. 13, 2013).
PillCam Capsule Endoscopy products by Given Imaging, http://www.givenimaging.com/en-int/Innovative-Solutions/Capsule-Endoscopy/Pages/default.aspx, available prior to Sep. 17, 2012.
Lehman, A.C. et al., "Surgery with Cooperative Robots," Comput. Aided. Surg., 13(2), pp. 95-105 (Mar. 2008).
Cadeddu, J.A. et al., "Novel magnetically guided intra-abdominal camera to facilitate laparoendoscopic single site surgery: initial human experience," Surg. Endoscopy, 23, pp. 1984-1899 (May 9, 2009).
C. S. Bell, K. L. Obstein, P. Valdastri, "Image partitioning and illumination in image-based pose detection for teleoperated flexible endoscopes", Artificial Intelligence in Medicine, 2013, in press.
M. Beccani, C. Di Natali, L. Sliker, J. Schoen, M. E. Rentschler, P. Valdastri, "Wireless Tissue Palpation for Intraoperative Detection of Lumps in Soft Tissue", IEEE Transactions on Biomedical Engineering, 2013, in press.
M. Simi, G. Gerboni, A. Menciassi, P. Valdastri, "Magnetic Torsion Spring Mechanism for a Wireless Biopsy Capsule", ASME Journal of Medical Devices, 2013, in press.
A. Arezzo, A. Menciassi, P. Valdastri, G. Ciuti, G. Lucarini, M. Salerno, C. Di Natali, M. Verra, P. Dario, M. Morino, "Experimental assessment of a novel robotically-driven endoscopic capsule compared to traditional colonoscopy", Digestive and Liver Disease, 2013, vol. 45, N. 8, pp. 657-662.
C. Di Natali, M. Beccani, P. Valdastri, "Real-Time Pose Detection for Magnetic Medical Devices", IEEE Transactions on Magnetics, 2013, vol. 49, N. 7, pp. 3524-3527.
M. Simi, R. Pickens, A. Menciassi, S. D. Herrell, P. Valdastri, "Fine tilt tuning of a laparoscopic camera by local magnetic actuation: Two-Port Nephrectomy Experience on Human Cadavers", Surgical Innovation, 2013, vol. 20, N. 4, pp. 385-394.
J. L. Gorlewicz, S. Battaglia, B. F. Smith, G. Ciuti, J. Gerding, A. Menciassi, K. L. Obstein, P. Valdastri, R. J. Webster III, "Wireless Insufflation of the Gastrointestinal Tract", IEEE Transactions on Biomedical Engineering, 2013, vol. 60, N. 5, pp. 1225-1233.
T. Horeman, D. D. Kurteva, P. Valdastri, F. W. Jansen, J. J. van den Dobbelsteen, J. Dankelman, "The Influence of Instrument Configuration on Tissue Handling Force in Laparoscopy", Surgical Innovation, 2013, vol. 20, N. 3, pp. 260-267.
M. Simi, M. Silvestri, C. Cavallotti, M. Vatteroni, P. Valdastri, A. Menciassi, P. Dario, "Magnetically Activated Setroscopic Vision System for Laparoendoscopic Single Site Surgery", IEEE/ASME Transactions on Mechatronics, 2013, vol. 18, N. 3, pp. 1140-1151.
K. L. Obstein, S. Battaglia, B. F. Smith, J. S. Gerding, P. Valdastri, "Novel approach for colonic insufflation via an untethered capsule (with video)", Gastrointestinal Endoscopy, 2013, vol. 77, N. 3, pp. 516-517.
K. Obstein, P. Valdastri, "Advanced Endoscopic Technologies for Colorectal Cancer Screening", World Journal of Gastroenterology, 2013, vol. 19, N. 4, pp. 431-439.
P. Valdastri, M. Simi, R. J. Webster III, "Advanced Technologies for Gastrointestinal Endoscopy", Annual Review of Biomedical Engineering, 2012, vol. 14, pp. 397-429.
G. Ciuti, N. Pateromichelakis, M. Sfakiotakis, P. Valdastri, A. Menciassi, D. P. Tsakiris, P. Dario, "A wireless module for vibratory motor control and inertial sensing in capsule endoscopy", Sensors and Actuators A: Physical, 2012, vol. 186, pp. 270-276.
P. Valdastri, G. Ciuti, A. Verbeni, A. Menciassi, P. Dario, A. Arezzo, M. Morino, "Magnetic air capsule robotic system: Proof of concept of a novel approach for painless colonoscopy", Surgical Endoscopy, 2012, vol. 26, N. 5, pp. 1238-1246.
G. Ciuti, M. Salerno, G. Lucarini, P. Valdastri, A. Arezzo, A. Menciassi, M. Morino, P. Dario, "A Comparative Evaluation of Control Interfaces for a Robotic-Aided Endoscopic Capsule Platform", IEEE Transactions on Robotics, 2012, vol. 28, N. 2, pp. 534-538.
M. Simi, N. Tolou, P. Valdastri, J. L. Herder, A. Menciassi, P. Dario, "Modeling of a Compliant Joint in a Magnetic Levitation System for an Endoscopic Camera", Mechanical Sciences, 2012, vol. 3, pp. 5-14.
M. Salerno, G. Ciuti, G. Lucarini, R. Rizzo, P. Valdastri, A. Menciassi, A. Landi, P. Dario, "A discrete-time localization method for capsule endoscopy based on on-board magnetic sensing", Measurement Science and Technology, 2012, 23 015701 (10pp).
C. Cavallotti, P. Merlino, M. Vatteroni, P. Valdastri, A. Abramo, A. Menciassi, P. Dario, "An FPGA-based flexible demo-board for

(56) References Cited

OTHER PUBLICATIONS endoscopic capsule design optimization", Sensors and Actuators A: Physical, 2011, vol. 172, No. 1, pp. 301-307.
M. Silvestri, M. Simi, C. Cavallotti, M. Vatteroni, V. Ferrari, C. Freschi, P. Valdastri, A. Menciassi, P. Dario, "Autostereoscopic Three-Dimensional Viewer Evaluation Through Comparison With Conventional Interfaces in Laparoscopic Surgery", Surgical Innovation, 2011, vol. 18, No. 3, pp. 223-230.
P. Valdastri, E. Sinibaldi, S. Caccavaro, G. Tortora, A. Menciassi, P. Dario, "A novel magnetic actuation system for miniature swimming robots", IEEE Transactions on Robotics, 2011, vol. 27, No. 4, pp. 769-779.
V. Pensabene, P. Valdastri, S. Tognarelli, A. Menciassi, A. Arezzo, P. Dario, "Mucoadhesive film for anchoring assistive surgical instruments in endoscopic surgery: in vivo assessment of deployment and attachment", Surgical Endoscopy, 2011, vol. 25, No. 9, pp. 3071-3079.
P. Valdastri, E. Susilo, T. Forster, C. Strohhöfer, A. Menciassi, P. Dario, "Wireless implantable electronic platform for chronic fluorescent-based biosensors", IEEE Transactions on Biomedical Engineering, 2011, vol. 58, No. 6, pp. 1846-1854.
M. Vatteroni, P. Valdastri, A. Sartori, A. Menciassi, P. Dario, "Linear-logarithmic CMOS pixel with tunable dynamic range", IEEE Transactions on Electron Devices, 2011, vol. 58, No. 4, pp. 1108-1115.
S. Tognarelli, V. Pensabene, S. Condino, P. Valdastri, A. Menciassi, A. Arezzo, P. Dario, "A pilot study on a new anchoring mechanism for surgical applications based on mucoadhesives", Minimally Invasive Therapy & Allied Technologies, 2011, vol. 20, No. 1, pp. 3-13.
M. Piccigallo, U. Scarfogliero, C. Quaglia, G. Petroni, P. Valdastri, A. Menciassi, P. Dario, "Design of a novel bimanual robotic system for single-port laparoscopy", IEEE/ASME Transactions on Mechatronics, 2010, vol. 15, No. 6, pp. 871-878.
M. Vatteroni, D. Covi, C. Cavallotti, P. Valdastri, A. Menciassi, P. Dario, A. Sartori, "Smart optical CMOS sensor for endoluminal applications", Sensors and Actuators A: Physical, 2010, vol. 162, No. 2, pp. 297-303.
D. Covi, C. Cavallotti, M. Vatteroni, L. Clementel, P. Valdastri, A. Menciassi, P. Dario, A. Sartori, "Miniaturized digital camera system for disposable endoscopic applications", Sensors and Actuators A: Physical, 2010, vol. 162, No. 2, pp. 291-296.
E. Buselli, V. Pensabene, P. Castrataro, P. Valdastri, A. Menciassi, P. Dario, "Evaluation of friction enhancement through soft polymer micro-patterns in active capsule endoscopy", Measurement Science and Technologies, 2010, 21 105802 (7pp).
P. Valdastri, C. Quaglia, E. Buselli, A. Arezzo, N. Di Lorenzo, M. Morino, A. Menciassi, P. Dario, "A Magnetic Internal Mechanism for Camera Steering in Wireless Endoluminal Applications", Endoscopy, 2010, vol. 42, pp. 481-486.
J. L. Toennies, G. Tortora, M. Simi, P. Valdastri, R. J. Webster III, "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.
M. Simi, G. Ciuti, S. Tognarelli, P. Valdastri, A. Menciassi, P. Dario, "Magnetic link design for a robotic laparoscopic camera", Journal of Applied Physics, 2010, vol. 107, No. 9, pp. 09B302-09B302-3.
M. Simi, P. Valdastri, C. Quaglia, A. Menciassi, P. Dario, "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.
G. Ciuti, R. Donlin, P. Valdastri, A. Arezzo, A. Menciassi, M. Morino, P. Dario, "Robotic versus manual control in magnetic steering of an endoscopic capsule", Endoscopy, 2010, vol. 42, pp. 148-152.
G. Ciuti, P. Valdastri, A. Menciassi, P. Dario, "Robotic magnetic steering and locomotion of capsule endoscope for diagnostic and surgical endoluminal procedures", Robotica, 2010, vol. 28, No. 2, pp. 199-207.
R. Carta, G. Tortora, J. Thoné, B. Lenaerts, P. Valdastri, A. Menciassi, R. Puers, P. Dario, "Wireless powering for a self-propelled and steerable endoscopic capsule for stomach inspection", Biosensors and Bioelectronics, 2009, vol. 25, No. 4, pp. 845-851.
C. Quaglia, E. Buselli, R. J. Webster III, P. Valdastri, A. Menciassi, P. Dario, "An Endoscopic Capsule Robot: A Meso-Scale Engineering Case Study", Journal of Micromechanics and Microengineering, 2009, vol. 19, No. 10, 105007 (11pp).
G. Tortora, P. Valdastri, E. Susilo, A. Menciassi, P. Dario, F. Rieber, M. O. Schurr, "Propeller-based wireless device for active capsular endoscopy in the gastric district", Minimally Invasive Therapy & Allied Technologies, 2009, vol. 18, No. 5, pp. 280-290.
E. Susilo, P. Valdastri, A. Menciassi, P. Dario, "A Miniaturized Wireless Control Platform for Robotic Capsular Endoscopy Using Advanced Pseudokernel Approach", Sensors and Actuators A: Physical, 2009, vol. 156, No. 1, pp. 49-58.
C. Cavallotti, M. Piccigallo, E. Susilo, P. Valdastri, A. Menciassi, P. Dario, "An Integrated Vision System with Autofocus for Wireless Capsular Endoscopy", Sensors and Actuators A: Physical, 2009, vol. 156, No. 1, pp. 72-78.
P. Valdastri, R. J. Webster III, C. Quaglia, M. Quirini, A. Menciassi, P. Dario, "A New Mechanism for Meso-Scale Legged Locomotion in Compliant Tubular Environments", IEEE Transactions on Robotics, 2009, vol. 25, No. 5, pp. 1047-1057.

* cited by examiner

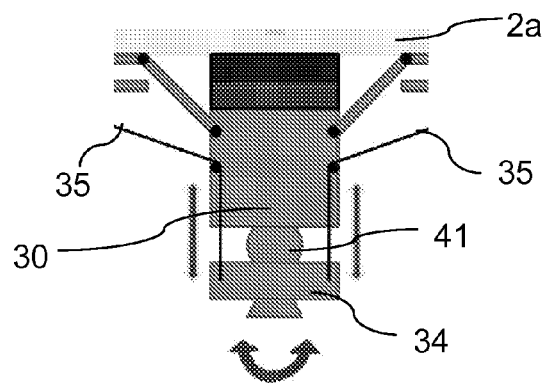
Fig. 6  Tilt y
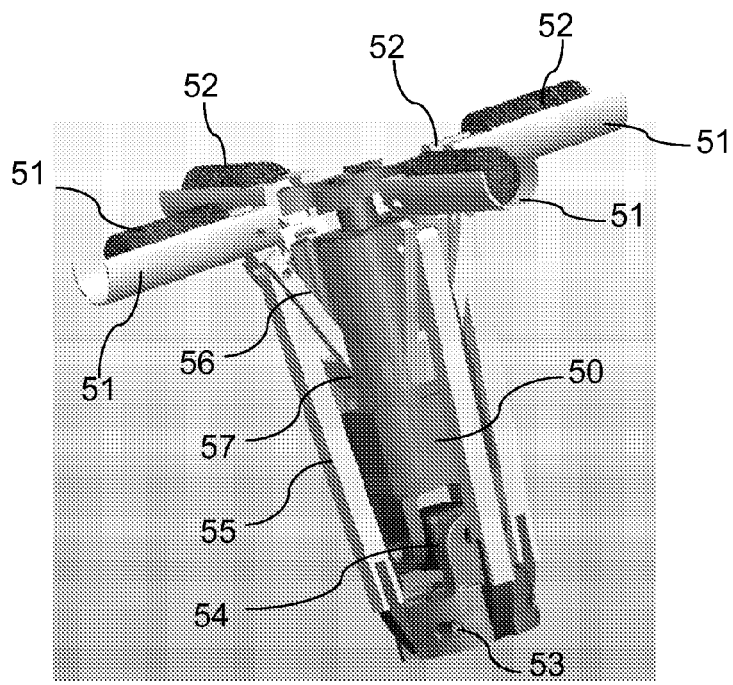
Fig. 7a
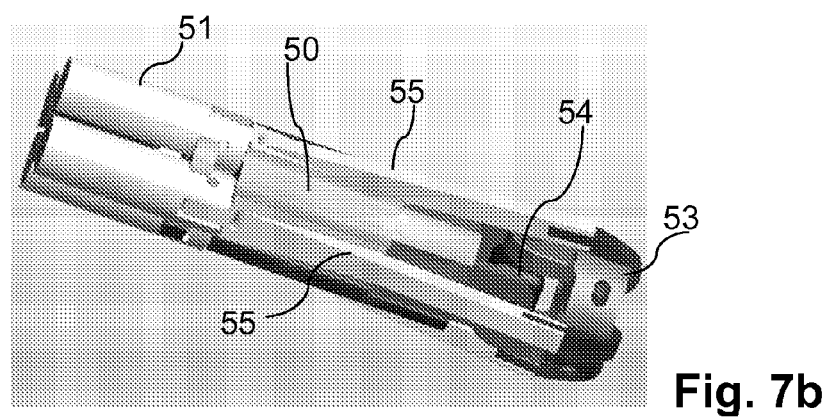
Fig. 7b

ROBOTIC PLATFORM FOR MINI-INVASIVE SURGERY

RELATED APPLICATIONS

This patent application is a national stage filing under 35 U.S.C. §371 of International Application No. PCT/IB2012/052739, filed on May 31, 2012, which claims priority to Italian Application No. FI2011A000114, filed on May 31, 2011. Priority to each application is hereby claimed, and the contents of each application are incorporated herein by reference.

FIELD OF THE INVENTION

The present invention refers in general to the field of the robotic platforms for mini-invasive surgery with a single access and more precisely it refers to a robotic platform for surgery comprising a trans-abdominal magnetic actuation for transferring degrees of freedom to endoscopic devices inside the patient's body.

STATE OF THE ART

In conventional surgery procedures, or in open surgery, the surgeon operates the patient making extended incisions. In such procedures the surgeon directly operates on the surgery target, manually or by means of conventional surgical instruments and has a direct visual and tactile feedback. The main disadvantage of the conventional surgical procedures however lies in its high invasiveness, which leads to relatively long hospitalisation periods and possible post-surgery complications for the patient.

The subsequent evolutions in the surgery procedures have developed towards the reduction of invasiveness thanks to minimally invasive surgery (MIS) techniques.

In the laparoscopic surgery techniques, the surgeon uses laparoscopic instruments for operating in the insufflated abdominal cavity passing through transcutaneous ports called trocar. Three to five small incisions (typically from 8 mm to 12 mm, sometimes from 3 mm up to 15 mm) are made in the body of the patient; an access is used for the endoscopic vision, while the others are required for surgery or assistance instruments. Laparoscopic instruments are actuated externally by the very surgeon. From the surgeon's point of view, the laparoscopic procedure is more complex with respect to the conventional surgery in that the visual and tactile feedback is mediated by the laparoscopic instruments. The working space of the laparoscopic instruments is also bound to the insertion of the latter through the trocars.

Most of the limitations of laparoscopic surgery were resolved by using teleoperated surgical robots. Intuitive Surgical, USA—thanks to its Da Vinci robot (see for example WO 00/30548)—is the leading manufacturer of robotic platforms for laparoscopic surgery.

Such system is based on the same principle of conventional laparoscopic surgery with the difference lying in the fact that the laparoscopic instruments are managed by a slave unit. The surgeon controls the slave unit through a console (master).

Use of robotics allows such platform to be more intuitive for the surgeon due to the possibility of having a stereoscopic vision, a scaling of the work space, a more intuitive control (compensation of the fulcrum effect) and a greater dexterity. However, such system still reveals numerous drawbacks that make it solely suitable for selected and particular procedures due to the high costs, the long times of preparation, the overall dimensions of the external robotic arms, the increase of invasiveness with respect to standard laparoscopic procedures (a total of five holes with a 12 mm hole, three 8 mm holes and a 5 mm hole) and the lack of a force feedback.

Alternative methods were proposed with the aim of further reducing the level of invasiveness.

NOTES (Natural Orifice Transluminal Endoscopic Surgery) is an alternative technique. Flexible endoscopes are used in this case: therefore, the connection between the surgeon and the surgery target is no longer mediated by a rigid connection. The endoscope is introduced through the natural orifices of the patient thus definitely eliminating the surface scars. The instruments are introduced through the operative channels of the endoscope. However, such procedure reveals drawbacks related to limited flexibility of the endoscope, the low dexterity and a limited feedback for the surgeon. Better results may be obtained with by using robotic endoscopes in which the actuation is carried onboard the endoscope itself. The Oleynikov and Farritor group of the University of Nebraska has developed robots with on-board actuation which can be introduced through natural orifices or a single abdominal port and which are then fixed to the abdomen through magnetic link means. Externally, the surgeon—through a suitable console—is capable of performing simple surgery tasks. Another possible endoluminal approach is that proposed by the Applicant in WO2010046823 where robotic serpents with actuators on-board are introduced into the stomach and they form two independent robotic units for bimanual operations. Each robotic unit is made up of three support legs and an operative arm.

The use of a robot in vivo with on-board actuation leads to considerable advantages in terms of the low invasiveness and flexibility, but it reveals drawbacks related to lack of a rigid support capable of allowing exerting the required forces to a manipulation for surgical tasks, and the low power given that all actuators are arranged on-board the robot. Given that the robot has to pass through natural gaps or through a single access port (e.g. the umbilical one), its diameter must be necessarily small, hence small motors are required. Small motors have low power and they are not capable of guaranteeing the performance of the Da Vinci system in terms of tractive force and motion speed of the instrument.

Single Port Laparoscopy (SPL) is another surgery technique. It represents an evolution of the conventional laparoscopic surgery in which there is used a single access port usually at the umbilical level and typically 2 or 3 cm wide, through which all the instruments required for the surgical operation are made to pass through. This leads to a considerable reduction of the invasiveness of the surgery procedure. The number of holes available for the operating instruments, the work space that can be used by the surgeon for manoeuvring as well as the possibility of triangulation, are all inevitably small.

Such drawbacks are overcome by using a robot suitable for the SPL procedures. An example of such type of robot is that described in WO2010042611, in which there are two robotic arms and a stereoscopic camera, independent and wire-actuated. An alternative version, still actuated externally, is described in WO20070146987. In the Italian patent application FI2010A000075 on behalf of the Applicant there is described an SPL robotic system, where the actuators regarding the distal degrees of freedom are all housed on-board the arm. However, in these cases the required access hole measures 2 or 3 cm, given that the space for the kinematic chain, which allows the movement of the robotic arms, is required.

In the field of robotic surgery there is strongly required the need of further reducing the invasiveness with respect to the current robots for robotic surgery, without jeopardizing the dexterity, power and degrees of freedom.

The current robotic solutions for surgery procedures are localised in defined access points (where the access ports or trocars are located) and require anyway more invasive incisions with respect to the conventional laparoscopic procedures (of the order of 1 cm, against the 2 or 3 cm required by the SPL procedures). Alternative solutions such as NOTES with the use of in vivo robots do not guarantee, in terms of performance, an efficient alternative to the currently used laparoscopic surgery procedures. On the other hand robotic SPL approaches however require a relevant incision and they are generally constrained to a working space proximal to the access port.

Robotic systems for mini-invasive surgery have also been proposed, in which there is provided a magnetic anchoring between internal manipulators and an external handle: concerning this see US2008/0058835; D. Oleynikov et al. *Comp. Aided Surg.*, 2008, (13), pages 95-105; and Cadeddu J. A. et al., *Surg. End.*, 2009, (23), pages 1894-1899. However, in these systems the coupling between external and internal magnets is solely used for anchoring, drawing and magnetic positioning of the system. Another non-robotised magnetic position and control system of a laparoscopic device is described in US2003/114731. Cadeddu J. A. et al., *J. Urology*, 2007, (178), pages 288-291 describes the use of a trans-abdominal platform prototype system for anchoring and magnetically guiding laparoscopic instruments by manipulating the external magnets; however, the control is not robotised. Simi M. et al., *J. Appl. Phys.*, 2010, (107), pages 1-3, lastly describe a laparoscopic camera prototype which—by actuating internal magnets—generates the viewpoint tilt.

SUBJECT OF THE INVENTION

The general subject of the present invention is to provide a robotic platform for mini-invasive surgery, in particular of the bimanual type with single access port, capable of guaranteeing a degree of dexterity, mechanical stability, power, reliability, comparable to a standard robotic platform for laparoscopic surgery, but characterised by a much lower invasiveness.

A particular subject of the present invention is to provide a robotic platform of the aforementioned type in which each robotic arm operating within the body of a patient is connected to an external control system by means of a reliable trans-abdominal magnetic coupling.

A further subject of the present invention is to provide a robotic platform of the aforementioned type, that allows positioning, anchoring and controlling several robotic arms within the body of a patient inserted through a single access trocar.

A further subject of the present invention is to provide a robotic platform of the aforementioned type, in which it is possible to reposition the robotic arms within the body of the patient without restrictions related to the trans-abdominal access points.

A further subject of the present invention is to provide a robotic platform of the aforementioned type, which is able to actively transfer degrees of freedom to inner robotic arms by actuating external magnetic means, without causing any deformation the patient abdomen wall.

These subjects are attained with the bimanual robotic surgery platform with single-access according to the present invention, whose essential characteristics are indicated in claim 1. Further important characteristics are indicated in the dependent claims.

The robotic platform for mini-invasive surgery according to the present invention is based on the idea of considering the robot positioned within a body cavity, such as the abdomen of a patient, introduced through a single access port, as an extension of external robotic manipulators actuatable by an operator, also from a remote position. The functional continuity between the external and internal robot is guaranteed by means of a magnetic link through the body wall delimiting said cavity between the internal, integral robot and the external one. The magnetic coupling not only guarantees a stable anchoring, but most of all it provides additional degrees of freedom to the internal robot, thus reducing the number of actuators present on-board the latter. Internal robots can also be repositioned without requiring further incisions on the wall of the body cavity: the internal manipulators can be translated over the entire wall using the external manipulators, thus providing a working space not restricted to the point of insertion and theoretically unlimited.

Preferably, the robotic platform according to the invention is used for mini-invasive surgery operations involving the abdominal region. At least three external robotic arms (for example having six degrees of freedom each, used both for the initial positioning of the internal robotic arms and for constituting, in association with the latter, a single element, controlled in real time, dedicated to perform a given surgery task) are used externally. An external robotic arm is used for supporting and possibly moving an internal auxiliary robotic arm carrying a vision system, while other external robotic arms are used for moving associated internal operative robotic arms. The internal robotic arms (both the auxiliary one for the vision and the operative ones) have a small diameter such that they can all pass through a single 12-15 mm trocar and terminate with a base on which there are provided magnets for supporting and actuating the arms. On the end-effector (operative end) of the external robotic arms there is provided a magnetic system dual to the internal one, such that, following a movement of the magnets of the system, there occurs a variation of the associated magnetic field which generates a corresponding variation of the position of the magnets placed therein and magnetically coupled thereto. This allows not only obtaining the anchoring and drawing the robotic manipulator on the insufflated abdomen of the patient but also the actuation of degrees of freedom by means of a suitable movement of the magnets. The inner magnets, mounted into dedicated mechanisms, are free to be moved (rotate/translate) by the interaction with the external magnetic field variations (rotation/translation), thus directly transmitting their motion to the internal robotic arms. In particular, the movement of the magnets of the external magnetic system can be obtained both by moving the end-effector of the external robotic arm and by providing these magnets with an autonomous movement. According to a preferred embodiment of the present invention this autonomous movement of the magnets of the external magnetic system allows the magnets to move autonomously and independently from each other; this movement may be achieved by using remotely controlled motors.

The proposed solution provides for a simple access trocar in the body of the patient having a small diameter (12-15 mm) with respect to what is provided for in the SPL surgery procedures (2 or 3 cm). This considerably minimises the number of incisions required and above all the invasiveness of the surgery procedure. The hole can be made in any point depending on the needs of the surgery procedure. When the umbilicus is used as the access port, the procedure would not leave visible scars in the body of the patient guaranteeing advantages also from an aesthetic point of view.

A fundamental advantage of the proposed solution is to overcome the need of a mechanical continuity in the robotic platform between internal and external parts thereof, by using a magnetic link between a robotic arm outside the patient and a robotic arm inside the body cavity. This also allows having a kinematic chain in which some degrees of freedom are actuated externally through a dedicated trans-abdominal magnetic link, while others are moved by actuators directly integrated in the internal robotic arm. Thus this allows a high dexterity (high number of degrees of freedom), without the need of having all the actuators on-board the internal robotic arm (this approach not being satisfactory in literature, given that it is possible to pass actuators having low power, and thus not capable of efficiently carrying out a high number of degrees of freedom, through an access port having a small diameter). Thus the internal robot is not only supported but it is also actuated by the magnetic link.

A further advantage consists in being able to reposition the internal robotic arms, both the operative ones and the one supporting the vision system, without restrictions due to trans-abdominal access points. Thus by still using a single abdominal access point, surgery operations in distinct quadrants may be performed, allowing fixing the various endoscopic devices at any point of the abdominal wall. These possibilities considerably increase the surgeons options maintaining to a minimum the level of invasiveness.

The control of the robotic platform according to the invention is in teleoperation. The surgeon—from a console—is capable of controlling intuitively the entire kinematic chain constituted by an external robotic arm, trans-abdominal magnetic coupling and internal robotic arm, as if it were a single robotic arm. In the calculation of the inverse kinematics the magnetic coupling is comprised; therefore, though at mechanical level the external robotic arm is not connected to the internal one, from a software point of view the user is capable of controlling it in a simple and intuitive manner, as if performing a conventional surgery operation.

BRIEF DESCRIPTION OF THE DRAWINGS

Further characteristics and advantages of the robotic platform for bimanual surgery with single access according to the present invention shall be clear from the description that follows of the embodiments thereof, provided solely by way of non-limiting example with reference to the attached drawings, wherein:

FIG. 6 shows a variant embodiment of a detail of the internal magnetic interface unit of the magnetic interface according to FIG. 5;

FIGS. 7a and 7b are perspective views of a further variant embodiment of the internal magnetic interface unit according to the embodiment schematically shown in FIG. 4, illustrated in open (operative) and closed state respectively;

DETAILED DESCRIPTION OF THE INVENTION

Figure 1:
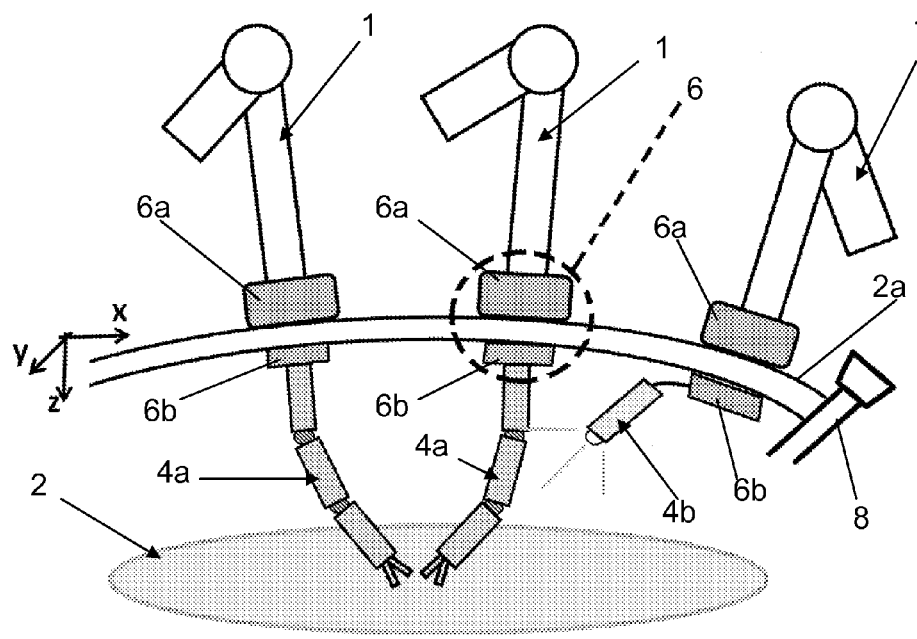
FIG. 1 is a schematic view of the robotic platform according to the invention.
Figure 2:
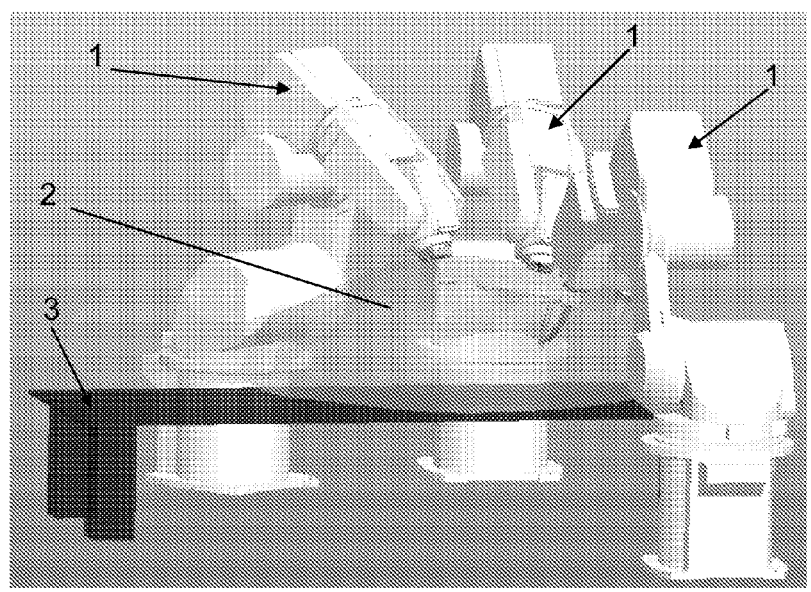
FIG. 2 is a simplified overall operative view of the robotic platform of FIG. 1.

With reference to FIGS. 1 and 2, the robotic platform for mini-invasive surgery according to the present invention comprises external robotic arms, generally indicated with 1, each preferably having six degrees of freedom, adapted to operate outside the body (in particular the abdomen) of a patient 2 arranged on a surgery plane 3, and internal robotic arms, generally indicated with 4a and 4b, able to be positioned within the body of the patient at the respective external robotic arms 1. The external robotic arms are of the commercial type, for example RV-6SL, the anthropomorphic industrial robotic arm with six degrees of freedom manufactured by Mitsubishi Electric.

Between each of the external robotic arms 1 and the respective internal robotic arms 4a, 4b, there is provided a trans-abdominal magnetic coupling system, generically indicated with 6, for anchoring and actuating the internal robotic arms 4a, 4b, and composed of an external magnetic interface unit 6a, mounted at the distal end constituting the end-effector of each external robotic arm 1, and of an internal magnetic interface unit 6b, mounted on the proximal end of each internal robotic arm 4a, 4b.

The external magnetic interface unit comprises magnetic elements, in particular permanent magnets or electromagnets; the internal magnetic interface unit comprises magnetic elements, preferably in form of permanent magnets.

The internal magnetic interface unit 6b of each internal robotic arm 4a, 4b is dual to the external magnetic interface unit 6a mounted on the corresponding external robotic arm 1. The term "dual" in the present description is used to identify a configuration of the end-effector of the external robotic arm comprising a number of magnets equivalent to the internal system, spatially arranged in the same manner as in the internal system. Depending on the various embodiments described hereinafter, such configuration may however reveal slight differences: in the passive case (FIG. 3) the magnets are constrained in a special fixed structure, in the translating case (FIGS. 5, 6, 7) the four magnets arranged radially around the central one may translate along the axes of the cross so as to be able to move the internal magnets, lastly, in the rotational case (FIGS. 8, 9) the magnets rotate around their own axis, instead of translating.

In the embodiment of the invention illustrated in FIGS. 1 and 2, the robotic platform comprises three external robotic arms 1 which, through the respective magnetic interfaces 6, control two internal operative robotic arms 4a and an auxiliary robotic arm 4b carrying a vision system 7, of the known type, comprising for instance a lighting unit and an image acquisition unit, such as a camera. A vision system suitable for the use in the robotic platform according to the present invention is for example the one described in the Italian patent application N. FI2010A000196, in the name of the Applicant.

In a preferred embodiment of the invention the internal robotic arms 4a,4b have a 12 mm diameter and they are adapted to be inserted into the abdomen of the patient through a single access port 8, for example constituted by a 12-15 mm trocar.

The internal operative robotic arms 4a have a modular design. Each arm is constituted by at least one module, provided with on-board actuation to confer it at least one degree of freedom, and by an end-effector possibly active, at the distal end thereof, required for the specific surgical function which it is intended to perform (e.g. forceps, scalpel, etc). Preferably each internal operative robotic arm is formed by two modules with at least 3 degrees of freedom and by an end effector. In a possible embodiment the degrees of freedom of each internal operative robotic arm, taken as a whole, are: six external degrees of freedom provided by the trans-abdominal actuation system and which can be used for the movement of the relative internal robotic arms 4a, 4b and three/four degrees of freedom of each of the internal operative robotic arms provided by the on-board actuators.

The degrees of freedom of an internal robotic arm in a possible embodiment can be Roll-Pitch-Roll (spherical wrist). Regarding the system of trans-abdominal magnetic coupling, there are transmitted up to six degrees of freedom: translation along three axes, pitch, yaw and rotation around the axes thereof (see for example FIG. 5)

Figure 3:
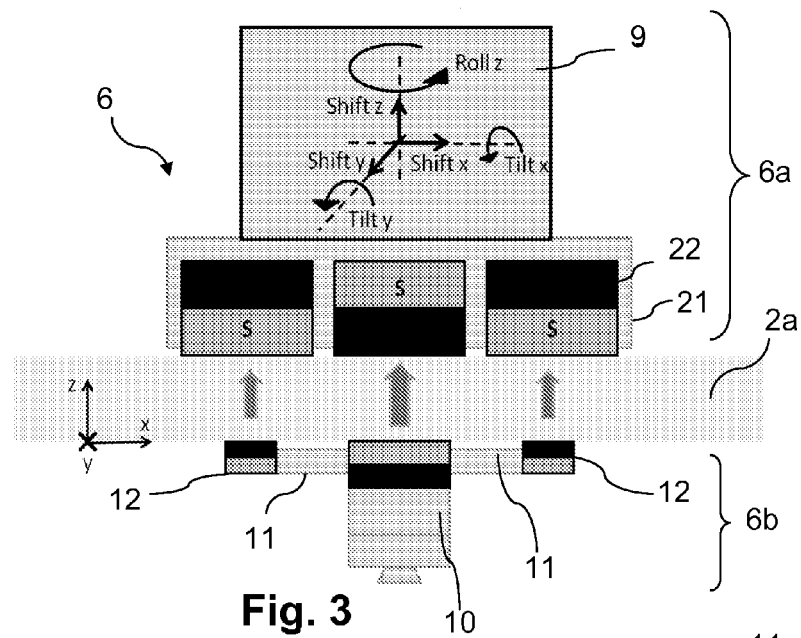
FIG. 3 schematically shows a first embodiment of a trans-abdominal magnetic interface of the robotic platform according to the invention.

FIG. 3 illustrates a first embodiment of the system of trans-abdominal magnetic coupling, or magnetic interface unit 6, of the robotic surgery platform according to the invention. The external magnetic interface unit is indicated with 6a and the internal magnetic interface unit separated from the abdominal wall 2a of the patient is indicated with 6b. The end effector, indicated with 9, arranged at the distal end of the external robotic arm 1, and a base 10 arranged at the proximal end of the internal robotic arm 4, are also shown in FIG. 3.

Figure 3A:
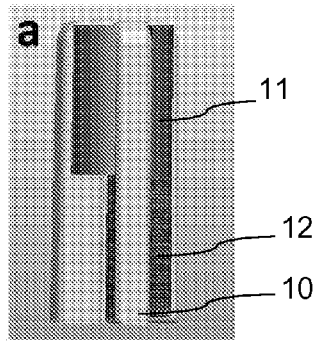
FIG. 3a,b illustrates an internal magnetic interface unit, in the closed and open state respectively, of the embodiment of FIG. 3.
Figure 3B:
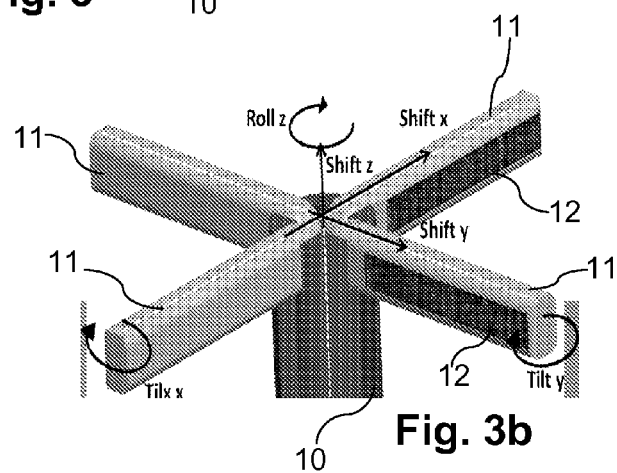
FIG. 3c schematically shows a possible system for opening and closing the arms carrying the magnets.

FIGS. 3a and 3b illustrate the internal magnetic interface unit 6b applied at the proximal end of each internal robotic arm 4a, 4b. The interface is formed by the aforementioned base 10 from which there are radially extended four angularly equally spaced arms 11 and carrying permanent magnets 12 fitted along the arms 11.

Figure 3C:
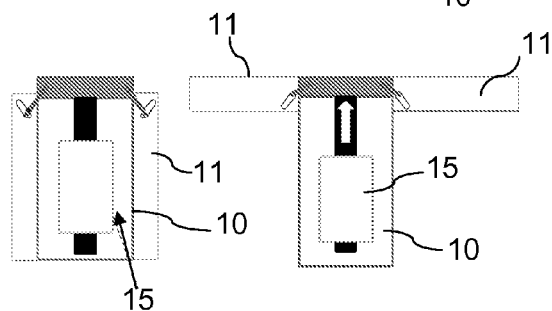

The arms 11 are rotatably connected to the base 10 so as to be enclosed thereon in seats 13 obtained therealong. In the closed state the interface and the associated robotic arm have dimensions such as to be able to pass through a 12-15 mm trocar and thus be able to be introduced into the insufflated abdomen of the patient. The opening and the closure of the arms 11 may be controlled by means of a suitable arrangement of the magnets 12, for example arranging the magnets so that in the closed form there are repulsive magnetic interactions therebetween. In the latter case the internal arm is forcedly inserted and pushed in closed form through the trocar with the help of a conventional laparoscopic instrument and subsequently upon overcoming the introduction port the arms are free to open. In order to facilitate the mechanism for the complete opening, it is necessary to position the internal magnetic interface at the external one. Magnetic docking is obtained in this manner. FIGS. 3a, 3b represent the case in which the aforementioned magnetic interaction is exploited to open the device. FIG. 3c instead schematically represents how to provide the system with an opening through linear actuation means. In this second case, an actuator 15 connected to the arms 11 through respective rods 16 is arranged in the base 10 for controlling the opening and closing of the arms 11. The rods 16 are rotatably connected both to the actuator and to the arms 11, hence, depending on the direction of motion of the actuator, they push the arms towards the opening position (FIG. 3b) or they pull them towards the closing position (FIG. 3a).

The external magnetic interface unit 6a is dual to the internal one and it has a cross-shaped configuration in which four arms 21, extending from a base 20, carry relative permanent magnets 22, as schematically shown in FIG. 3. The movement and the orientation of the end effector 9 allow transmitting six degrees of freedom to the internal robotic arm, as shown in FIGS. 3 and 3b, i.e. three rotations (roll z, rotation around the axis z perpendicular to the laying plane of the open arms; pitch and yaw, rotation around the axes x and y for aligning the arms two by two) and three translations (shift x, shift y and shift z, translations along the axis x, along the axis y and along the axis z, as defined above). In this case the magnets 12 mounted on the arms 11 provide both for anchoring and positioning the relative robotic arm.

Considering the degrees of freedom provided by the interface of magnetic coupling, the internal robotic arm has six degrees of freedom (Translation x, y, z, Roll z, Pitch x, y) provided from outside and three/four internal degrees of freedom provided by the on-board actuators.

If necessary a needle having a diameter below 3 mm (scarless) can be used for anchoring the internal magnetic interface unit to the respective external unit in a specific position. Thus, it is possible to increase the stability and also obtain more than the four degrees of freedom typical of the laparoscopic instruments.

Figure 4:
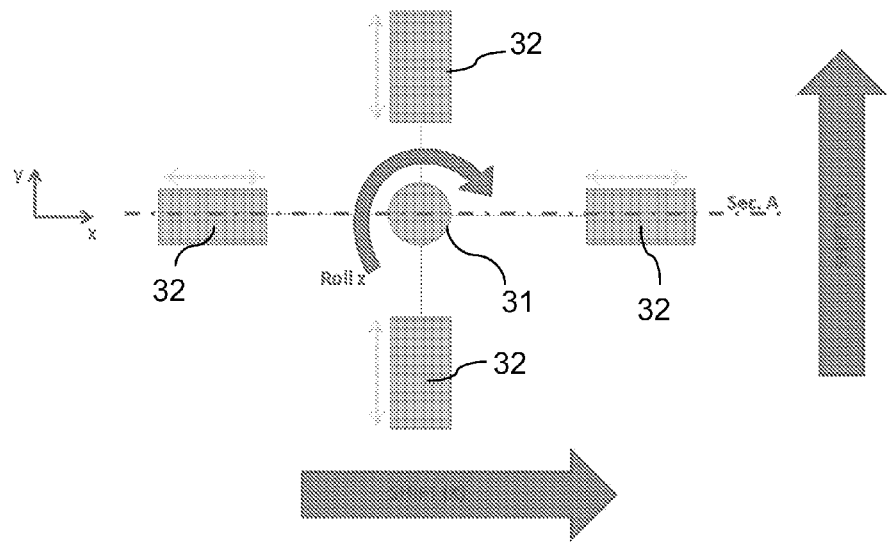
FIG. 4 illustrates—in plan view—a schematic view of a second embodiment of the trans-abdominal magnetic interface according to the invention.
Figure 5:
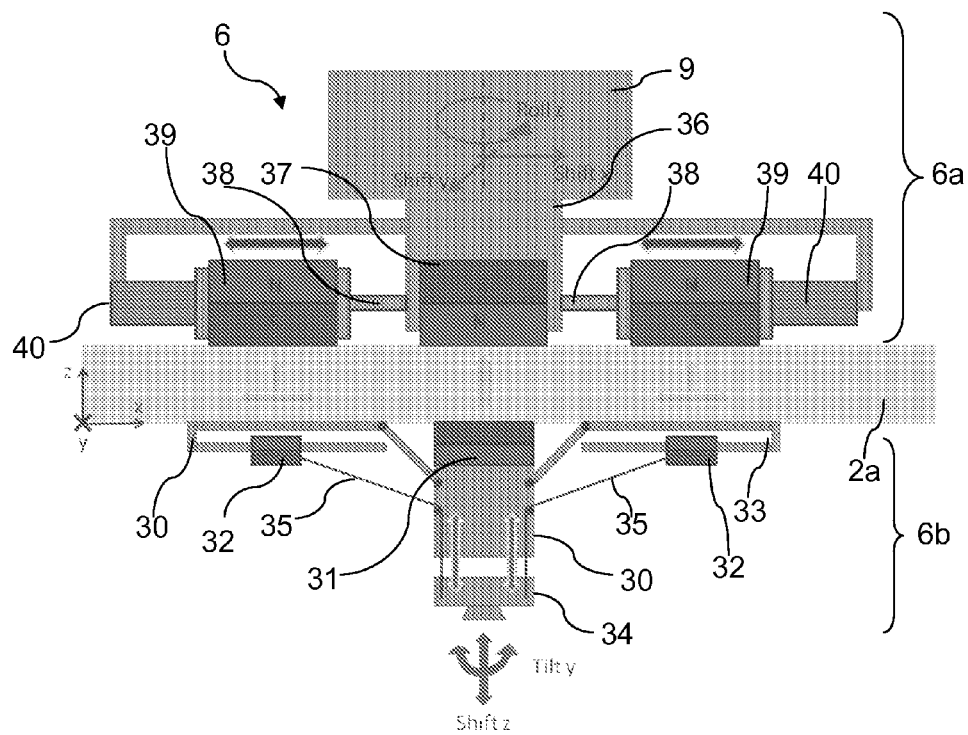
FIG. 5 is a transverse section schematic view of the magnetic interface of FIG. 4.

A second embodiment of the magnetic coupling system is illustrated in FIGS. 4 and 5. FIG. 4 is a schematic representation of the arrangement of the magnets provided on the internal interface unit 6b, and i.e. a central magnet 31 and four magnets 32 arranged radially and equally spaced, and shows the degrees of freedom (two translations (shift x, shift y), and a bearing rotation (roll z) transmittable from the external magnetic interface unit 6a dual to the unit 6b. FIG. 5 schematically illustrates the system of magnetic interface 6 provided for each pair of internal and external robotic arms with the external 6a and internal 6b interface units thereof. The internal magnetic interface unit 6b, arranged at the proximal end of the internal robotic arm, comprises a base 30 carrying the central magnet 31 with support and centring function and the four magnets 32, mounted on respective linear guides 33 with low friction arranged cross-like around the base 30, which allow actuating of the additional six degrees of freedom. The magnets 32 are connected to a plate 34 by means of respective cables 35 and the plate 34 is fixed at the proximal end of a respective internal robotic arm. Correspondingly the external magnetic interface unit 6a comprises a base 36, fixed at the end-effector 9 of the external robotic arm, carrying a central magnet 37. From the base 36 there are radially extended equally spaced four linear guides 38 with low friction on which there are slidably mounted respective magnets 39. The sliding of the magnets 39 is controlled by actuators 40 of the conventional type.

The dual configuration of the external 6a and internal 6b magnetic interface unit allows, moving the magnets 39 along the respective guides 38, the corresponding magnets 32 to move in the same way. The movement of the four magnets 32 along the guides 33 determines the tractive force of the respective cables 35, integral with the magnets 32, and thus a corresponding movement of the plate 34. More precisely, the movement of a pair of opposite magnets in the same direction, determines the orientation of the plate 34 around the aligning axis of the other pair of magnets (tilt x or tilt y), while the actuation of the four magnets simultaneously approaching or moving away produces a translation of the internal robotic arm along the axis z (shift z). Furthermore the translation of the entire end-effector of the external robotic arm, to which the external magnetic interface unit 6a is integral, causes a corresponding displacement of the internal robotic arm to obtain further two degrees of freedom fundamental for positioning the device on the abdominal wall (shift x, shift y). Lastly rotating the end-effector with respect to the axis of the external robotic arm also allows obtaining the degree of freedom roll z. In conclusion exploiting such system allows obtaining up to six degrees of freedom without requiring to include specific actuators on the internal robotic arm.

With the aim of guaranteeing greater stability and integrally constrain the motion of the internal modular arm it is possible to connect the plate 34 to the base 30 with joint-like articulation means 41, such as a spherical or cardanic joint, as shown in FIG. 6. This allows gaining in terms of accuracy and reliability, but to the detriment of the possibility of sliding along the axis z.

Even in this embodiment the linear guides 33 of the internal interface unit 6b can be closed on the base 30 as previously described to allow the introduction of the internal robotic arm into the body of the patient through the trocar.

The transmission means of the movement from the slidable magnet of the internal magnetic interface unit to the internal robotic arm may also be constituted by rigid articulated transmissions provided by means of rigid rods. A solution of this type is shown in FIGS. 7a and 7b. While the external magnetic interface unit 6a is identical to that illustrated in FIG. 5 and thus it is not illustrated in the aforementioned figures for the sake of simplicity, the internal magnetic unit interface 6b comprises a base 50 from which there are extended four radially equally-spaced arms 51. On each of the arms 51 there is fixed a respective permanent magnet 52. The base 50 is connected to a plate 53, fixed at the proximal end of the internal robotic arm, through a cardanic joint 54. For each radial arm 51 there are provided two rods 55 and 56 hinged in a common position thereof with an end thereof. The rod 55 is also hinged with the other end thereof to the plate 53, while the rod 56 is rotatably engaged slidably in a guide 57 obtained longitudinally on the base 50.

In this embodiment the four magnets 52 are intended to be positioned directly at contact with the abdomen of the patient and to slide therealong following corresponding sliding of the magnets present in the associated external magnetic interface unit 6a, which axially translate the respective arms 51. The translation of the magnets 52 actuates the cardanic joint 54 through the articulation constituted by the rods 55 and 56. The degrees of freedom of this system are the same of the previous one with the difference lying in the fact that also the opening and closing system is passive, i.e. it is controlled by the sliding of the arms 51. Actually, when the magnets are at the internal end of the radial arms 51, i.e. the one closest to the base 50, also the arms are folded on the extension thereof and the two rods 55 and 56 are laid on the base 50. Also in this case, in the closed position the magnets tend to repel through magnetic repulsion. During the insertion through the trocar, the arms are forcedly held at contact by the dimension of the rigid operative channel and, upon exceeding the port, the arms are free to be deployed.

Figure 8:
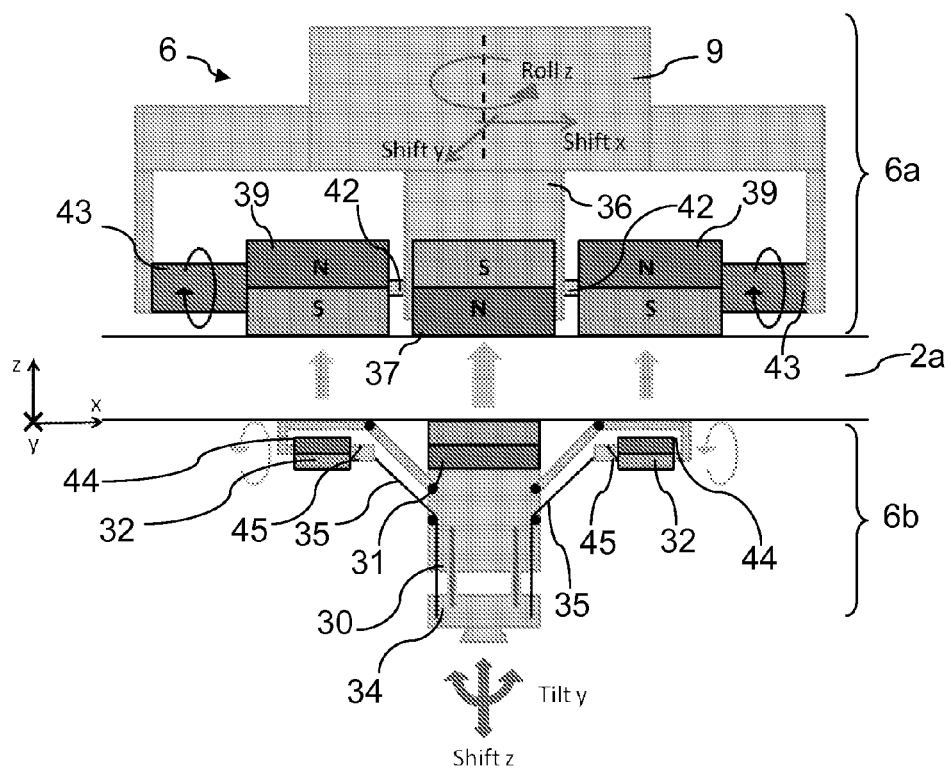
FIG. 8 is a transverse section schematic view of a third embodiment of the magnetic interface of the robotic platform according to the invention.

In a different embodiment of the invention the actuation of the cables 35 is not induced by the translation of the magnets 32, but by their rotation. As shown in FIG. 8, where components identical to those of the embodiment illustrated in FIG. 5 have the same reference number, the magnets 39 of the external magnetic interface unit 6a are mounted on axes 42 extending radially equally spaced from the base 36 carrying the central magnet 37 and connected to actuators 43 of the conventional type adapted to rotate them. The corresponding magnets 32 of the internal magnetic interface unit 6b are rotatably mounted on axes 44 extending radially equally spaced from the base 30 and they are integral with guides 45 on which the ends of the cables 35 are wound. The rotation of the magnets 39 of the external magnetic interface unit 6a induces a rotation of the corresponding magnets 32 of the internal magnetic interface unit 6b and of the guides 45 integral thereto causing the winding or the unwinding of the cables 35. The movements which can be transmitted to the internal robotic arm are equal to those described in the previous embodiment of the invention and i.e. oscillation around the axes x and y and translation along the axis z.

Figure 9:
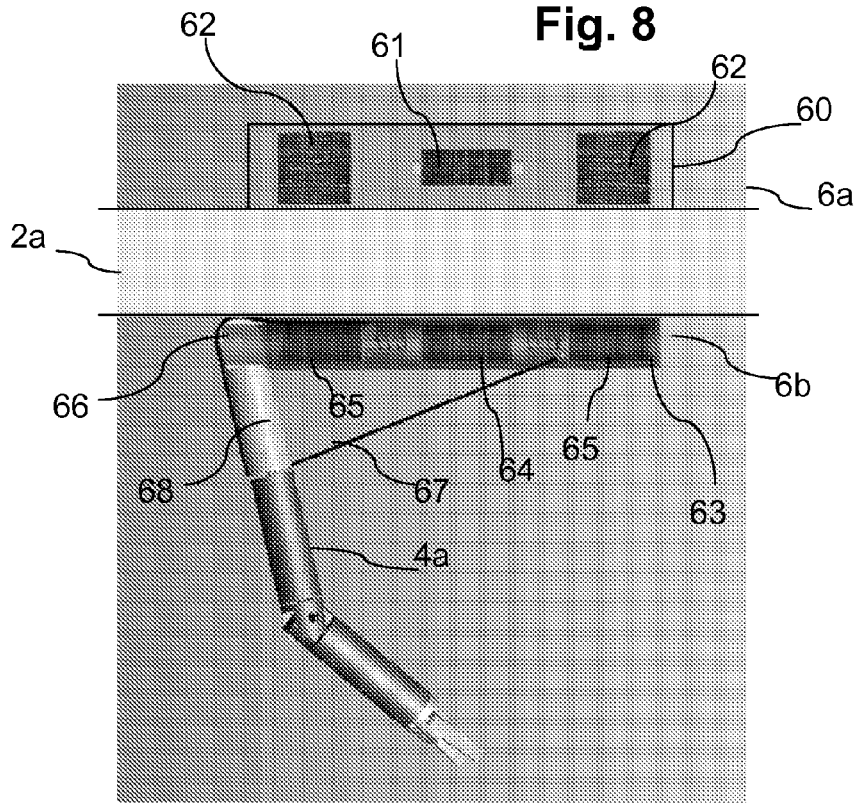
FIG. 9 is a transverse section schematic view of a fourth embodiment of the magnetic interface of the robotic platform according to the invention.
Figure 11:
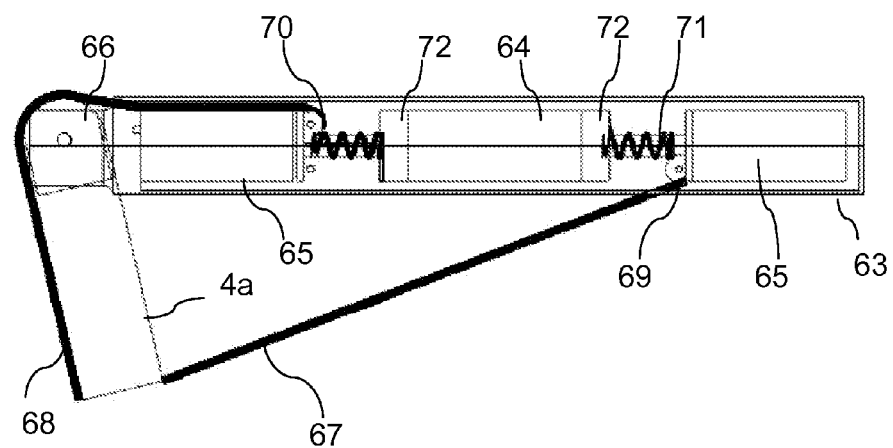
FIG. 11 shows a detailed view of the internal magnetic interface unit of FIGS. 9 and 10.

In the embodiment of the magnetic interface 6 illustrated in FIG. 9 each external magnetic interface unit 6a comprises three permanent magnets including a central one 61 and two end ones 62 housed in an external support structure 60 integral with the end-effector of the related external robotic arm. As shown in FIGS. 9 and 11, each internal robotic arm is provided with an internal magnetic interface unit 6b, dual of the external one, comprising an internal support structure 63, connected at the proximal end of the internal robotic arm, in which there are arranged a central magnet 64 and two end magnets 65. The internal support structure 63 is substantially tubular-shaped having a diameter equal to that of the internal robotic arm to which it is connected through a rotoidal joint 66. The magnets 62 located at the ends of the external support structure 60 are designated to generate forces on the end magnets 65 corresponding in the internal support structure 63, with the aim of maintaining the latter adherent to the abdominal wall, while the central magnet 61 in the external support structure 60 is used for inducing a rotational motion to the corresponding central magnet 64 of the internal support structure 63. The rotation induced on the internal central magnet 64 actuates a mechanism with cables 67, 68 and pulleys 69, 70 which allows the rotation of the internal robotic arm around the joint 66. More precisely, the cables 67 and 68 are wound in the opposite direction on an axis integral with the rotatable magnet 64, hence they operate in an antagonist manner on the arm 4a, given that the tractive force of one of them is compensated by the loosening of the other. The external magnetic interface unit 6a, being integral with the end-effector of the external robotic arm, may be moved along the abdominal surface conferring further two degrees of freedom (shift x, shift y).

In order to improve the stability of the tubular structure 63 in case of forces generating a moment along the axis X, there can be provided suitable structures (not shown) directly integrated in the tubular structure itself, as lateral fins. Alternatively, to the tubular structure 63 there can be coupled additional stabilization structures, using conventional laparoscopic instruments (forceps) for orthogonally hooking them to the tubular structure.

Figure 10:
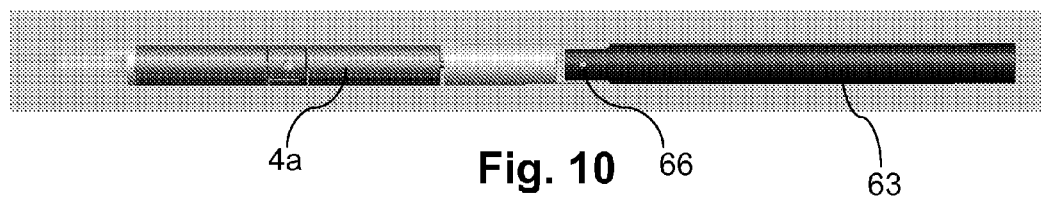
FIG. 10 is a longitudinal view of the internal magnetic interface unit and of the relative internal robotic arm in aligned condition along the common longitudinal axis.

FIG. 10 shows the internal robotic arm with the associated internal support structure 63 aligned thereto. Such configuration allows a simple insertion of the robotic arm in the abdomen through a single umbilical trocar.

In the detailed view of FIG. 11 there is shown the central magnet 64 integral with an axis 71 rotatably mounted on supports 72 integral with the tubular structure 63. The two cables 67 and 68 are wound in opposite directions on the axis 71 and oriented through the respective pulleys 69 and 70 so that the respective free ends thereof can be fixed to the robotic arm on diametrically opposite parts. In this manner, inducing a rotation in a direction of the magnet 64, one of the two cables is tensioned and the other is loosened, causing the rotation of the robotic arm around the joint 66 in one direction or in the opposite one.

The removal of the internal robotic arms at the end of a surgery intervention is carried out using conventional laparoscopic instruments. The internal robotic arm is initially approached to the hole from which it will be extracted (trocar) starting from the distal part. The external magnetic support is thus removed and the internal device is gradually closed even using a conventional laparoscopic instrument (e.g. forceps). In particular, for the removal of an internal magnetic interface with radial structure, the closure may be motorised or alternatively forced into the inlet in the trocar also during the extraction. In the case of the embodiment of FIG. 9 the device is realigned to the hole and extracted in the configuration of FIG. 10. In case of application of stabilisation accessories, they will be de-coupled from the tubular structure first and then extracted.

The control of the robotic platform and in particular of the trans-abdominal magnetic link, with the aim of being able to perform the required movements in an extremely accurate, dextrous and safe manner, involves the sensorization of some parameters as the intensity of the magnetic field, position and relative orientation between the magnetic interfaces, with the aim of evaluating possible misalignment in the drawing of the internal trans-abdominal magnetic interface with respect to the external one. By means of the relative positions of the magnets adapted for the actuation, with the aim of having a control feedback on the procedure, there is provided a low level feedback control so as to be able to compensate misalignment during the movement between the two internal and external magnetic interfaces.

The magnets used in the present invention have a diametric polarization and they can be of the N52 type, Neodymium-Iron-Boron type, or the like, of cylindrical shape.

From what has been described above, it is clear that the robotic platform for mini-invasive surgery according to the present invention fully achieves the predetermined purposes.

The presence of a trans-abdominal magnetic coupling overcomes the need of providing mechanical continuity between the external control system and the internal robotic arms. The described system does not require a trocar for each inserted instrument, thus avoiding the problem of having to perform additional incisions in case of need to reposition the surgical instruments. However, in the same manner the passive actuation—through trans-abdominal magnetic coupling—allows overcoming the problem lying in requiring using small actuators and thus with poor performance in terms of developed force. This allows that an actual alternative to conventional surgery robotic systems is guaranteed.

The internal operative robotic arms and the robotic arm carrying the vision system are introduced, in succession, through a single 12-15 mm trocar. This makes the robotic platform as minimally invasive not only with respect to the conventional laparoscopic surgery platforms, but also with respect to more innovative SPL systems. The change of surgical instruments may be simply carried out by replacing an internal robotic arm with another one carrying a different instrument.

The robotic platform according to the present invention provides the surgeon with a very flexible system offering an extremely high number of degrees of freedom for performing a surgery task. The total number of degrees of freedom of the robotic platform is actually given by that of the external robotic arms, that of the relative magnetic couplings and that of the internal robotic arms. Such flexibility offers the surgeon the possibility to always have, when operating, the best conditions for the surgery task solution.

Thus, the robotic platform according to the invention can be used as a replacement or integration for the current systems of laparoscopic surgery. In addition, it allows considerably reducing the invasiveness of the laparoscopic procedure, using a single hole of considerably small dimensions with respect to the other single port solutions. However, the platform maintains the intuitiveness and the advantages of using robotics in surgery additionally guaranteeing greater flexibility due to the considerable number of degrees of freedom and the possibility of repositioning on the abdomen of the patient. Due to these reasons the proposed system may also lead to the creation of new surgery protocols.

The robotic platform according to the invention as described above allows performing bimanual robotic surgery operations, but it is clear that more than two internal operative robotic arms can be used for performing complex surgery tasks. In any case, access to the abdomen remains single and mainly used for the passage of cables for power supplying the motors or the cameras integrated in the internal robotic arms.

Though the present description refers to the use of the robotic platform according to the invention in mini-invasive surgery interventions involving the abdominal region, it should be borne in mind that the use thereof can be extended to other body cavities.

The robotic platform for mini-invasive surgery according to the present invention may be subjected to variants and/or modifications without departing from the scope of protection of the invention as defined in the attached claims.

The invention claimed is:

1. A robotic system for minimally invasive surgery, the system comprising:
   a plurality of internal robotic arms configured for insertion in a body cavity of a patient through a single access port;
   a plurality of external robotic arms positioned externally to the patient with each external robotic arm associated with one of the internal robotic arms; and
   a magnetic coupling system comprising
      a plurality of external magnetic interface units, each external magnetic interface unit associated with one of the external robotic arms,
      a plurality of internal magnetic interface units, each internal magnetic interface unit associated with one of the internal robotic arms, and wherein movement of one of the external robotic arms controls a corresponding movement of the associated internal robotic arm through the magnetic coupling system, wherein each of the plurality of external magnetic interface units include a magnet and each of the plurality of internal magnetic interface units include a magnet, such that movement of one of the magnets in one of the external magnetic interface units is transmitted to the magnet of the corresponding internal magnetic interface unit through variations of the magnetic fields generated between the magnets of the respective magnetic interface units, and wherein the movement is further transmitted to the internal robotic arm associated with the internal magnetic interface unit, wherein the magnet of each of the plurality of the external magnetic interface units are arranged on radial arms extending from a base at a distal end of a respective one of the external robotic arms and the magnet of each of the plurality of internal magnetic interface units are arranged on radial arms extending from a base at a proximal end of a respective internal robotic arm.

2. The robotic system according to claim 1, wherein the magnet of each of the plurality of the external magnetic interface units are controlled to move autonomously and independently from each other.

3. The robotic system according to claim 1, wherein the radially extending arms are aligned two by two.

4. The robotic system according to claim 1, wherein the magnets are fixed to the radially extending arms.

5. The robotic system according to claim 1, wherein the radially extending arms are axially movable relative to the base.

6. The robotic system according to claim 1, wherein the magnets are pivotably mounted on the radially extending arms.

7. The robotic system according to claim 1, wherein the magnets are slidably mounted on the radially extending arms.

8. The robotic system according to claim 7, wherein the magnets of the internal magnetic interface units are connected to a plate integral to the corresponding internal robotic arm through transmission means for the transmission of motion to the corresponding internal robotic arm.

9. The robotic system according to claim 8, further comprising a joint between the plate and the base, the joint being actuated by the transmission means.

10. The robotic system according to claim 8, wherein the transmission means is flexible.

11. The robotic system according to claim 10, wherein the transmission means comprises wires connected to respective magnets and submitted to tractive force following a movement of the magnets.

12. The robotic system according to claim 8, wherein the transmission means is articulatably rigid.

13. The robotic system according to claim 12, wherein the rigid transmission means comprise, for each internal robotic arm, a pair of rods hinged at one of their ends to the internal robotic arm, the other ends being hinged respectively to a guide axially sliding on the base and to articulated joint means placed between the base and the plate.

14. The robotic system according to claim 1, wherein the radially-extending arms of the internal magnetic interface units are foldable on the base and an actuator is connected to the radially-extending arms and configured to arrange the radially-extending arms in an open state after insertion of the internal robotic arm into the body cavity.

15. The robotic system according to claim 1, wherein arrangement of the magnets on the radially extending arms of the internal magnetic interface unit is such that, in the folded state on the base, a repulsive magnetic force is generated which is contrasted once the internal robotic arms are inserted in the body cavity and is suitable to deploy the radially extending arms in an opened state.

16. The robotic system according to claim 1, wherein the external magnetic interface unit and the associated internal magnetic interface unit each comprise a stationary permanent magnet.

17. The robotic system according to claim 1, wherein the external magnetic interface units and the internal magnetic interface units comprise one of magnetic field sensors, linear/angular position sensors, accelerometers, gyroscopes, for monitoring non-alignments between the external magnetic interface units and the internal magnetic interface units to balance the non-alignments due to the movements by integrating the data coming from the sensors in a feedback control cycle.

* * * * *